United States Patent [19]

Berry

[11] 4,175,090
[45] Nov. 20, 1979

[54] CHEMICAL COMPOSITION

[75] Inventor: David Berry, North Humberside, England

[73] Assignee: BP Chemicals Limited, London, England

[21] Appl. No.: 880,476

[22] Filed: Feb. 23, 1978

[51] Int. Cl.$^2$ ................................................ C07F 1/08
[52] U.S. Cl. .................................. 260/438.1; 71/67; 424/294
[58] Field of Search ..................................... 260/438.1

[56] References Cited

U.S. PATENT DOCUMENTS

| | | | |
|---|---|---|---|
| 1,082,658 | 12/1913 | Somermeier | 424/140 X |
| 2,159,864 | 5/1939 | Serciron | 260/438.1 |
| 2,434,402 | 1/1948 | Flur | 260/429.9 X |
| 2,444,945 | 7/1948 | Morrell | 260/438.1 X |
| 2,604,485 | 7/1952 | Booker et al. | 260/438.1 X |
| 2,824,886 | 2/1958 | Barry et al. | 260/438.1 |
| 3,900,504 | 8/1975 | Woerner | 260/438.1 |
| 4,020,180 | 4/1977 | Woerner | 260/438.1 |

OTHER PUBLICATIONS

Grossman, Chem. Abst., 7, 2523$^4$ (1913).
Gauthier, Chem. Abst., 54, 16247e, (1960).

*Primary Examiner*—Helen M. S. Sneed
*Attorney, Agent, or Firm*—Brooks, Haidt, Haffner & Delahunty

[57] ABSTRACT

This invention relates to a method of preparing cuprammonium carboxylate complexes in solution and the use of such solutions as a fungicide for treating wood, painted surfaces, fabrics and to inhibit algal growth.

2 Claims, No Drawings

CHEMICAL COMPOSITION

The present invention relates to compositions containing cuprammonium complexes of carboxylic acids and a method of preparing such compositions.

Copper salts have long been used in fungicidal compositions. Furthermore, the toxicity of soluble copper salts is also well recognised. Whilst it is possible to produce solid copper compounds of moderate and acceptable toxicity levels, the use of such solid compounds even in very fine form is limited to a considerable extent due to the difficulties in applying such solids uniformly on a substrate surface to achieve maximum surface cover for effective protection per unit weight of the compound. Even in cases where such copper compounds have been produced in soluble form, such solutions have been very dilute solutions containing more than 60% by weight of the solvent for about 8% of effective copper content. Such compositions in the context of cuprammonium carboxylate have been claimed and described in U.S. Pat. Nos. 3,900,504 and 4,020,180. Such solutions present a different kind of problem, i.e. that of bulk handling which makes them commercially unviable and futhermore, the limited solubility of these complexes generate additional problems due to precipitation and sedimentation in the containers used for transportation. In commercial operations, such precipitation can also lead to blockages in pumping and spraying equipment.

It has now been found that homogeneous aqueous solutions of cuprammonium complexes may be produced which not only contain relatively smaller amounts of the solvent but also have a higher effective copper content than produced hitherto.

Accordingly, the present invention is a homogeneous liquid composition comprising a cuprammonium complex of one or more $C_1$ to $C_4$ monocarboxylic acids containing between 4 and 10% by weight of dissolved copper and up to 40% by weight of water.

According to a further embodiment, the present invention is also a method of preparing a homogeneous liquid composition comprising a cuprammonium complex of one or more $C_1$ to $C_4$ monocarboxylic acids containing between 4 and 10% by weight of dissolved copper and up to 40% by weight of water, said method comprising reacting an acid ammonium salt of the monocarboxylic acid with a copper compound selected from cuprous oxide and cupric oxide in the presence of aqueous ammonia.

The monocarboxylic acid moieties in the salt may be derived from saturated or unsaturated monocarboxylic acids. Examples of such acids include formic acid, acetic acid, propionic acid, the isomeric butyric acids, acrylic acid and methacrylic acid. By the expression "acid ammonium salt" as used here and throughout the specification is meant salts in which two moles of the acid moiety are present per mole of the ammonium ion on a chemical equivalent basis. Thus, the acid ammonium salts are preferably one or more of ammonium di-formate, ammonium di-acetate and ammonium di-propionate. The product of the reaction between the acid ammonium salt and the copper oxide in the presence of aqueous ammonia is a dark blue aqueous solution containing the cuprammonium complex in a concentration within the specified range.

The liquid compositions of the present invention possess fungicidal activity due to the presence of copper. These compositions therefore find several uses, for example as paint biocides, as wood preservatives, as fungicides to prevent mildew on fabrics and to counteract growth of algae and marine fouling. Particularly, these compositions inhibit the growth of fungi such as *Cladosporium herbarum* which are responsible for the spoilage of paints, and *Coniophora cerebella* which causes wood decay.

For any of the above uses, the compositions may be used as such in the form of their aqueous solution. The aqueous solution may however contain other conventional additives capable of supplementing their activity such as free formic acid, propionic acid, formalin and bisulphites. The aqueous solutions may additionally contain wetting, spreading or sticking agents or may be emulsified with mineral oils where necessary.

The concentration of the cuprammonium complex applied to a substrate will depend not only upon the substrate and its end use but also on the nature of the attack to be treated or prevented. These can however be easily ascertained by those skilled in the art. For example, for the preservation of wood, treatment rate equivalent to concentrations of copper in the range 0.4 to 1.0% may be used.

Where it is desirable to dilute the cuprammonium complex solution for high volume application, as for instance in the case of preservation of wood referred to above, the dilution is preferably carried out using a 1.3% aqueous ammonia solution to prevent precipitation of the complex. If water alone is used as diluent, for example at dilutions of about 100:1, a flocculent gelatinous blue precipitate may separate.

The cuprammonium complexes of the present invention have greater solubility in water than the conventional copper salts such as copper formate and copper propionate, and when prepared, have a pH of between 7 and 9. Their improved solubility allows a freerflow and more even spread of the composition onto the substrate, particularly when used as sprays. As can be seen from the table, compared to copper propionate and copper formate, the cuprammonium complexes are more water soluble which facilitates application by spraying. The differences in copper solubility (at ambient temperature) are presented below:

| Compound | %Cu in a saturated aqueous solution |
|---|---|
| Copper Propionate | 2.2 |
| Cuprammomium Propionate Complex | 5–10.0 |
| Copper Formate | 2.9 |
| Cuprammonium Formate Complex | 4.5 |

The invention is further illustrated with reference to the following Examples.

EXAMPLES

A. PREPARATION OF COMPLEXES

The complex can be prepared by reaction of the acid ammonium salt (70% w/w aqueous solution) with either cupric or cuprous oxide and aqueous ammonia. Some preparations are described below.

Cuprammonium Propionate Complex

1. A 70% aqueous solution of ammonium dipropionate (212 g) was added to cupric oxide (30 g), and the mixture heated under reflux for 30 minutes. After cooling 88 g of aqueous ammonia (33.3% w/w $NH_3$) was added, and the mixture filtered to give a dark blue solution containing 13.5% w/w $NH_3$, 39.8% w/w propionate, 7.0% w/w copper, and 39.7% w/w water (pH=8.0).

2. A 70% aqueous solution of ammonium dipropionate (106 g) was added to cupric oxide (30 g), and the mixture heated under reflux for 30 minutes. After cooling 44 g of aqueous ammonium (33.3% $NH_3$) was added, the solution recooled, and filtered to remove unreacted cupric oxide (6.6 g). The final solution contained 13.0% w/w $NH_3$, 38.2% w/w propionate, 10% w/w copper, and 38.8% w/w water (pH=8.0).

3. A 70% aqueous solution of ammonium dipropionate (212 g) was added to 30 g of cuprous oxide and heated under reflux for 1 hour. After cooling, 88 g of aqueous ammonia (33.3%) was added, the solution cooled, and filtered to remove excess copper metal (12 g). The final solution contained 14.0% w/w $NH_3$, 41.3% w/w propionate, 5.0% w/w copper, and 39.7% w/w water (pH=7.6).

Cuprammonium Formate Complex

4. This complex was prepared by reacting cupric oxide with aqueous ammonia and 70% aqueous ammonium diformate. The final solution contained 4.5% by weight copper, 40% by weight formate, and 39.0% by weight water.

B. ACTIVITY OF CUPRAMMONIUM COMPLEXES

Wood Preservative Activity

5. The complex in solution at various dilutions was run onto wooden blocks of Scots pine sapwood of the species *Pinus sylvestris* as follows:

The blocks were oven dried, weighed and vacuum impregnated with a solution of cuprammonium propionate. Twelve (12) blocks were treated at each of the following concentration of the complex in solution as % copper: 1.0, 0.63, 0.40, 0.25, 0.16, 0.10 and 0.063. The blocks thus treated along with untreated blocks were exposed to a culture of *Coniphora cerebella* organism in bottles containing soil for a period of six (6) weeks.

After this period the test blocks were removed from the culture, weighed, oven dried and reweighed. The final oven dried mass was compared with the initial dry mass to calculate the loss in mass due to decay by the organism. Two blocks treated at each concentration and not exposed to the organism were also oven dried and weighed to correct for the uptake of the preservative complex.

On the basis of weight loss, the toxic limit, i.e. the interval between that concentration which just permits decay and the concentration next highest in the series which inhibits all decay was 0.25-0.40% copper in the treating solution. The loading in the wood expressed as copper for this toxic limit was 1.9-3.2 $Kg/m^3$ of wood.

As a further comparison one of the most widely used waterborne preservatives based on copper sulphate, potassium dichromate and arsenic pentoxide known as 'CCA preservative' was tested as before using blocks of the same wood and the same organism. This gave a toxic limit of 1.8-3.0 $Kg/m^3$ in terms of metal content. Thus for a metal loading similar to that of CCA, the present invention enables the use of the more acceptable copper complexes.

Paint Biocide Activity

6. The activity of copper ammonium propionate as a paint biocide was evaluated as follows:

Copper ammonium propionate (500 ppm) was added to a molten medium (50° C.) consisting of Czapek Dox agar (Oxid CM 97) and poured into 100 mm Petri dishes and the mixture allowed to harden. Surface moisture was removed from the growth media by drying at 50° C. The agar plates were inoculated with suspensions of the test organisms using a multipoint inoculator, and incubated for seven (7) days at 25° C. A corresponding control medium without addition of the complex was prepared, inoculated and incubated under identical conditions. The following spore germination results were obtained. In all cases even the slightest growth or spore germination was considered to constitute a failure of the preservative to inhibit the organisms.

| | Test Organisms | | | |
|---|---|---|---|---|
| | *Cladosporium herbarum* | *Fusarium species* | *Penicillium expansum* | *Pestalotia macrotricha* |
| Cuprammonium propionate (500 ppm) | No germination | No germination | No germination | No germination |
| Control | Positive germination | Positive germination | Positive germination | Positive germination |

We claim:

1. A process for preparing a homogeneous liquid composition comprising a cuprammonium complex of one or more $C_1$-$C_4$ monocarboxylic acids containing between 4 and 10% by weight of dissolved copper and up to 40% by weight of water, said process comprising reacting an acid ammonium salt of the monocarboxylic acid with a copper compound selected from cupric oxide and cuprous oxide in the presence of aqueous ammonia.

2. A process for preparing cuprammonium complex according to claim 1 wherein the acid ammonium salt is selected from the group consisting of ammonium diformate, ammonium diacetate and ammonium dipropionate.

* * * * *